US00PP17612P2

(12) United States Plant Patent
Hynes

(10) Patent No.: US PP17,612 P2
(45) Date of Patent: Apr. 17, 2007

(54) ***LANTANA* PLANT NAMED 'MONIKE'**

(50) Latin Name: *Lantana camara*
Varietal Denomination: Monike

(75) Inventor: Michael J. Hynes, Venice, FL (US)

(73) Assignee: Monrovia Growers, Azusa, CA (US)

( * ) Notice: Subject to any disclaimer, the term of this patent is extended or adjusted under 35 U.S.C. 154(b) by 0 days.

(21) Appl. No.: 11/245,383

(22) Filed: Oct. 6, 2005

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
(74) *Attorney, Agent, or Firm*—C. A. Whealy

(57) ABSTRACT

A new and distinct cultivar of *Lantana* plant named 'Monike', characterized by its compact, upright and outwardly spreading plant habit; uniformly mounded plant form; freely branching habit and short internodes; dense and bushy form; freely and continuously flowering habit; and flowers that are initially yellow and become orange and eventually red purple in color with development.

1 Drawing Sheet

Botanical designation: *Lantana camara.*
Cultivar denomination: 'Monike'.

BACKGROUND OF THE INVENTION

The present Invention relates to a new and distinct cultivar of *Lantana* plant, botanically known as *Lantana camara,* and hereinafter referred to by the cultivar name Monike.

The new *Lantana* originated from a chance cross-pollination of the *Lantana camara* cultivar Moni, disclosed in U.S. Plant Pat. No. 1,478, as the female, or seed, parent with an unknown selection of *Lantana camara,* as the male, or pollen, parent. The new *Lantana* was selected as a single flowering plant from the resulting progeny of the chance cross-pollination by the Inventor in a controlled environment in Altadena, Calif. in the summer of 1994.

Asexual reproduction of the new cultivar by terminal cuttings in a controlled environment in Azusa, Calif., since the spring of 2002 has shown that the unique features of this new *Lantana* are stable and reproduced true to type in successive generations.

SUMMARY OF THE INVENTION

Plants of the cultivar Monike have not been observed under all possible environmental conditions. The phenotype may vary somewhat with variations in environment and culture such as temperature and light intensity, without however, any variance in genotype.

The following traits have been repeatedly observed and are determined to be the unique characteristics of 'Monike'. These characteristics in combination distinguish 'Monike' as a new and distinct *Lantana* cultivar:

1. Compact, upright and outwardly spreading plant habit; uniformly mounded plant form.
2. Freely branching habit and short internodes; dense and bushy form.
3. Freely and continuously flowering habit.
4. Flowers that are initially yellow and become orange and eventually red purple in color with development.

Plants of the new *Lantana* can be compared to plants of the female parent, the cultivar Moni. In side-by-side comparisons conducted in Azusa, Calif., plants of the new *Lantana* differed from plants of the cultivar Moni in the following characteristics:

1. Plants of the new *Lantana* were more compact than plants of the cultivar Moni.
2. Plants of the new *Lantana* and the cultivar Moni differed in leaf shape as plants of the cultivar Moni had ovate-shaped leaves.
3. Plants of the new *Lantana* and the cultivar Moni differed slightly in leaf coloration.
4. Plants of the new *Lantana* were more freely flowering than plants of the cultivar Moni.
5. Plants of the new *Lantana* and the cultivar Moni differed in flower coloration.

Plants of the new *Lantana* can also be compared to plants of the cultivar Robcomplan, disclosed in U.S. Plant Pat. No. 9,837. In side-by-side comparisons conducted in Azusa, Calif., plants of the new *Lantana* differed from plants of the cultivar Robcomplan in the following characteristics:

1. Plants of the new *Lantana* were larger and more vigorous than plants of the cultivar Robcomplan.
2. Plants of the new *Lantana* and the cultivar Robcomplan differed in leaf shape as plants of the cultivar Robcomplan had ovate-shaped leaves.
3. Plants of the new *Lantana* had larger leaves than plants of the cultivar Robcomplan.
4. Plants of the new *Lantana* and the cultivar Robcomplan differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Lantana.*

The photograph at the bottom of sheet comprises a side perspective view of a typical flowering plant of 'Monike' grown in a container.

The photograph at the top of the sheet comprises a close-up view of a typical inflorescence and leaves of 'Monike'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown in one-gallon containers in an outdoor nursery for about one year in Azusa, Calif. During the production of the plants, day temperatures ranged from about 24° C. to about 29° C. and night temperatures ranged from about 4° C. to about 12° C.

Botanical classification: *Lantana camara* cultivar Monike.

Parentage:

*Female, or seed, parent.*—*Lantana camara* cultivar Moni, disclosed in U.S. Plant Pat. No. 1,478.

*Male, or pollen, parent.*—Unknown selection of *Lantana camara,* not patented.

Propagation:

*Type cutting.*—Terminal cuttings.

*Time to initiate roots.*—About two weeks.

*Time to produce a rooted young plant.*—About three months.

*Root description.*—Fine, fibrous; initially glaucous white in color then becoming closer to tan with development.

*Rooting habit.*—Freely branching.

Plant description:

*Form.*—Flowering subshrub; upright and outwardly spreading plant habit; uniformly mounded plant form; compact growth habit. Freely branching; about five primary lateral branches each with lateral branches potentially forming at every node. Moderately vigorous.

*Plant height.*—About 17 cm.

*Plant diameter.*—About 30 cm by 48 cm.

*Lateral branches.*—Length: About 22 cm. Diameter: About 6 mm. Internode length: About 1.5 cm. Strength: Strong, but flexible. Texture: Rough, pubescent. Color: Young: Close to 146D. Woody: Close to 199A to 199B.

*Foliage description.*—Arrangement: Opposite; simple. Length: About 5.5 cm. Width: About 3.7 cm. Shape: Elliptic. Apex: Acuminate. Base: Acute to attenuate. Margin: Serrate. Texture, upper and lower surfaces: Leathery, rough, coarse; pubescent. Venation pattern: Pinnate, arcuate, reticulate. Color: Developing foliage, upper surface: Close to 146A. Developing foliage, lower surface: Close to 146B. Fully expanded foliage, upper surface: Close to 147A. Fully expanded foliage, lower surface: Close to 147B. Venation, upper surface: Close to 146B. Venation, lower surface: Close to 147C. Petiole length: About 1.6 cm. Petiole diameter: About 2 mm. Petiole texture, both surfaces: Pubescent. Petiole color, upper surface: Close to 146B. Petiole color, lower surface: Close to 146D.

Flower description:

*Flower type and habit.*—Small salverform flowers arranged in axillary umbels; flowers face mostly upward or outward. Flowers self-cleaning. Very freely flowering with potentially two inflorescences per node; typically about 24 flowers per umbel.

*Natural flowering season.*—Spring until frost in the autumn; flowering continuous.

*Flower longevity on the plant.*—About one week.

*Fragrance.*—None detected.

*Inflorescence diameter.*—About 3.7 cm.

*Inflorescence height.*—About 1.5 cm.

*Flowers.*—Appearance: Flared trumpet, corolla fused, four-parted; flowers roughly rectangular in shape. Diameter: About 9 mm by 11 mm. Corolla tube length: About 1.7 cm.

*Flower buds.*—Length: About 8 mm. Diameter: About 3 mm. Shape: Elongated. Color: Close to 180A.

*Corolla.*—Arrangement/appearance: Single whorl of four petals, fused into flared trumpet. Petal length from throat: Upper and lower petals: About 5 mm. Lateral petals: About 4 mm. Petal width: Upper and lower petals: About 6 mm. Lateral petals: About 5 mm. Petal shape: Spatulate to somewhat orbicular. Petal apex: Rounded, emarginate. Petal margin: Slightly serrate. Petal lobe texture, upper and lower surfaces: Smooth, velvety. Corolla throat and tube texture: Pubescent. Color: Petal lobes, when opening, upper surface: Close to 12B. Petal lobes, when opening, lower surface: Close to 12C to 12D. Petal lobes, fully opened, upper surface: Close to 21B becoming closer to 34C with development, eventually becoming close to 53B. Petals lobes, fully opened, lower surface: Close to 16C becoming closer to 32D with development. Throat: Close to 12B. Tube: Close to 52B.

*Calyx.*—Length: About 2.5 mm. Width: About 2 mm. Shape: Tubular. Apex: Acute. Base: Fused. Texture, upper and lower surface: Smooth, glabrous. Color, upper and lower surfaces: Close to 145A.

*Peduncles.*—Length: About 2.5 cm to 3 cm. Diameter: About 1.5 mm. Angle: About 45° from the stem. Strength: Flexible, but strong. Texture: Pubescent. Color: Close to 146B.

*Pedicels.*—Not observed, flowers not stalked.

*Reproductive organs.*—Stamens: Quantity/arrangement: Four per flower, adnate to floral tube. Anther shape: Oblong. Anther length: Less than 1 mm. Anther color: Close to 13B. Pollen amount: Scarce. Pollen color: Close to 13B. Pistils: Quantity: One per flower. Pistil length: About 4 mm. Stigma shape: Rounded. Stigma color: Close to 1A. Style length: About 2.5 mm. Style color: Close to 1C. Ovary color: Close to 144A to 144B.

*Seed/fruit.*—Seed and fruit development have not been observed.

Disease/pest resistance: Plants of the new *Lantana* grown in the garden have not been noted to be resistant to pathogens and pests common to *Lantana.*

Weather tolerance: Plants of the new *Lantana* have been observed to be very tolerant to rain and wind.

Temperature tolerance: Plants of the new *Lantana* have been observed to be tolerant to temperatures ranging from 0° C. to 38° C.

It is claimed:

1. A new and distinct cultivar of *Lantana* plant named 'Monike', as illustrated and described.

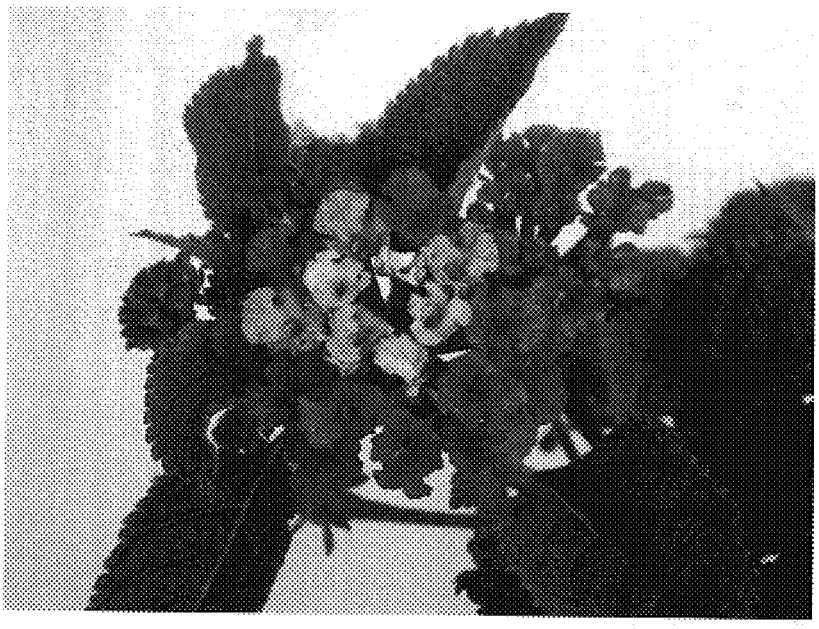
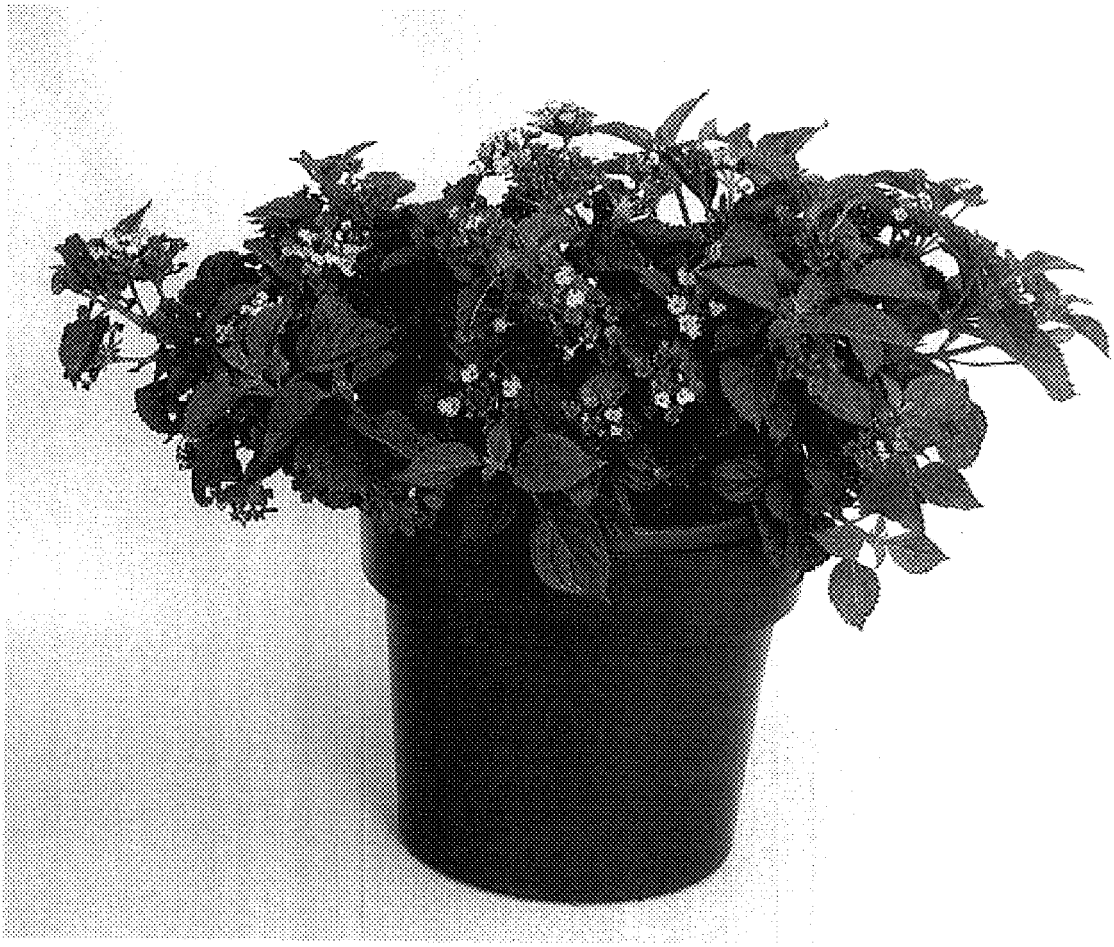

* * * * *